(12) United States Patent
Redel

(10) Patent No.: US 10,867,383 B2
(45) Date of Patent: Dec. 15, 2020

(54) DETERMINATION OF A CLINICAL CHARACTERISTIC USING A COMBINATION OF DIFFERENT RECORDING MODALITIES

(71) Applicant: Thomas Redel, Poxdorf (DE)

(72) Inventor: Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 645 days.

(21) Appl. No.: 15/687,295

(22) Filed: Aug. 25, 2017

(65) Prior Publication Data

US 2018/0061047 A1 Mar. 1, 2018

(30) Foreign Application Priority Data

Aug. 25, 2016 (DE) .......................... 10 2016 215 976

(51) Int. Cl.
*G06T 7/00* (2017.01)
*A61B 6/00* (2006.01)
(Continued)

(52) U.S. Cl.
CPC ............ *G06T 7/0012* (2013.01); *A61B 5/021* (2013.01); *A61B 5/026* (2013.01); *A61B 5/02007* (2013.01); *A61B 5/02028* (2013.01); *A61B 6/504* (2013.01); *A61B 6/5217* (2013.01); *A61B 6/5235* (2013.01); *G06T 7/11* (2017.01); *G06T 7/60* (2013.01); *G06T 11/003* (2013.01);
(Continued)

(58) Field of Classification Search
None
See application file for complete search history.

(56) References Cited

U.S. PATENT DOCUMENTS 9,706,925 B2 * 7/2017 Taylor ...................... G06T 7/74
9,858,387 B2 * 1/2018 Lavi .................... A61B 5/02007
(Continued)

FOREIGN PATENT DOCUMENTS

CN 103270513 A 8/2013
CN 103458790 A 12/2013
(Continued)

OTHER PUBLICATIONS

German Office Action for German Application No. 102016215976.3, dated May 18, 2017.
(Continued)

*Primary Examiner* — Anand P Bhatnagar
(74) *Attorney, Agent, or Firm* — Lempia Summerfield Katz LLC

(57) ABSTRACT

A method for determining a clinical characteristic of a body vessel segment including providing, to a computing device, a three-dimensional reconstruction of a body vessel containing the body vessel segment. A segmented angiography recording of the body vessel segment is provided to the computing device. The computing device extracts at least one global feature of the body vessel from the three-dimensional reconstruction and extracts at least one local feature of the body vessel segment from the angiography recording. The clinical characteristic is determined for the body vessel segment as a function of the at least one extracted local feature and the at least one extracted global feature.

18 Claims, 1 Drawing Sheet

(51) Int. Cl.
*G06T 11/00* (2006.01)
*G06T 7/11* (2017.01)
*A61B 5/02* (2006.01)
*A61B 5/021* (2006.01)
*A61B 5/026* (2006.01)
*G06T 7/60* (2017.01)
*A61B 5/055* (2006.01)
*A61B 6/03* (2006.01)

(52) U.S. Cl.
CPC ............ *G06T 11/008* (2013.01); *A61B 5/055* (2013.01); *A61B 6/032* (2013.01); *A61B 6/481* (2013.01); *A61B 6/487* (2013.01); *G06T 2200/04* (2013.01); *G06T 2200/08* (2013.01); *G06T 2207/10081* (2013.01); *G06T 2207/10088* (2013.01); *G06T 2207/20081* (2013.01); *G06T 2207/30104* (2013.01); *G06T 2211/404* (2013.01)

(56) References Cited

U.S. PATENT DOCUMENTS

| | | | | |
|---|---|---|---|---|
| 9,977,869 | B2* | 5/2018 | Lavi | .................... G06F 19/3437 |
| 10,559,388 | B2* | 2/2020 | Lavi | ...................... G06F 19/321 |
| 2010/0053209 | A1 | 3/2010 | Rauch | |
| 2012/0041301 | A1 | 2/2012 | Redel | |
| 2013/0211728 | A1 | 8/2013 | Taylor | |
| 2014/0003688 | A1 | 1/2014 | Hansis | |
| 2015/0342551 | A1 | 12/2015 | Lavi | |
| 2015/0356753 | A1* | 12/2015 | Lauritsch | .............. G06T 7/0016 382/130 |
| 2016/0073970 | A1* | 3/2016 | Sharma | .................. A61B 6/507 600/431 |
| 2018/0061114 | A1 | 3/2018 | Redel | |
| 2018/0206808 | A1 | 7/2018 | Grass | |
| 2019/0150869 | A1* | 5/2019 | Passerini | ............... A61B 6/5217 |
| 2019/0304592 | A1* | 10/2019 | Ma | ........................ G06T 7/0012 |
| 2019/0333216 | A1* | 10/2019 | Isgum | ................... G06K 9/6269 |

FOREIGN PATENT DOCUMENTS

| | | |
|---|---|---|
| CN | 105190630 A | 12/2015 |
| DE | 102010039312 A1 | 2/2012 |
| DE | 102011003929 A1 | 8/2012 |
| DE | 102014210591 A1 | 12/2015 |
| WO | WO2016008837 A1 | 1/2016 |

OTHER PUBLICATIONS

Morris, Paul D., et al. ""Virtual" (computed) fractional flow reserve: current challenges and limitations." JACC: Cardiovascular Interventions 8.8 (2015): 1009-1017.

Chinese Office Action for Chinese Application No. 201710740449.5 dated Apr. 26, 2020, with English translation.

* cited by examiner

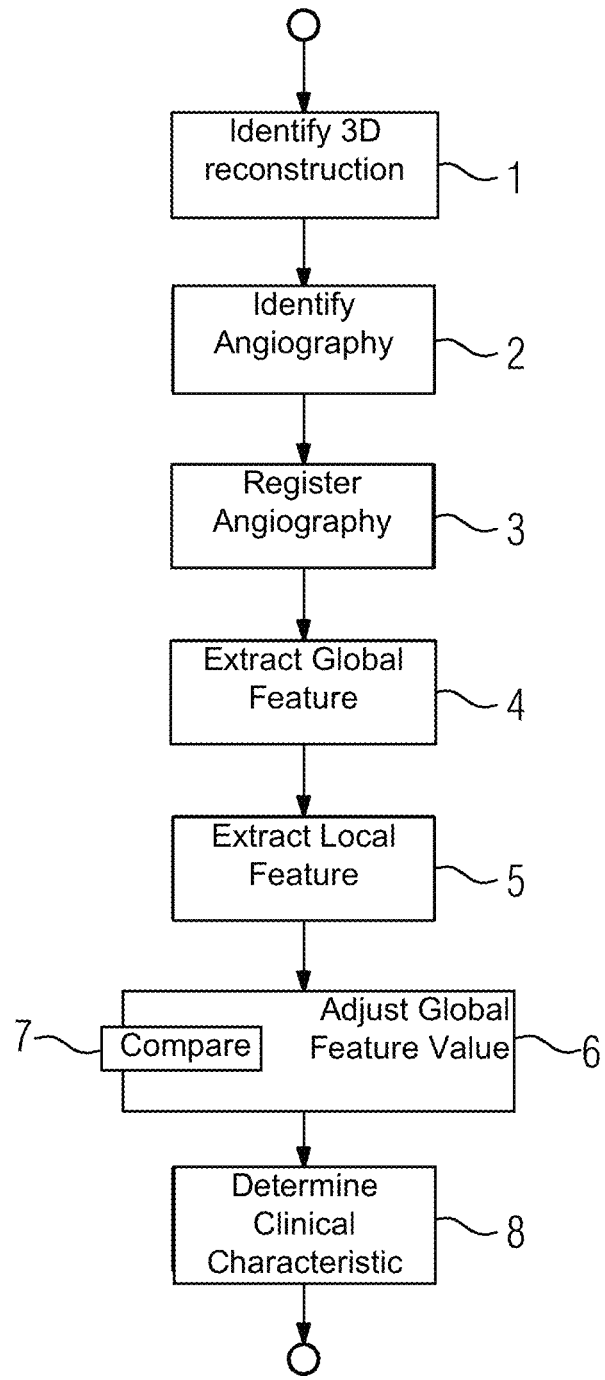

DETERMINATION OF A CLINICAL CHARACTERISTIC USING A COMBINATION OF DIFFERENT RECORDING MODALITIES

This application claims the benefit of DE 10 2016 215 976.3, filed on Aug. 25, 2016, which is hereby incorporated by reference in its entirety.

BACKGROUND

The present embodiments relate to determining a clinical characteristic of a body vessel segment.

An established clinical characteristic is the fractional flow reserve (FFR), which, for example, may be measured using a pressure wire. The pressure wire is guided past a stenosis in the body vessel or body vessel segment, where the pressure is determined distally to the stenosis. This distal pressure is divided by the proximal pressure to calculate the fractional flow reserve.

It is possible, using a three-dimensional model of the body vessel segment or body vessel section in which the stenosis is contained, and further, basic conditions such as, for example, the blood flow in milliliters per second through the body vessel segment, to calculate the pressure flow via the stenosis using mathematical methods of fluid dynamics (e.g., computational fluid dynamics). A virtual value for the fractional flow reserve, a virtual FFR value, may also be calculated based virtually on the three-dimensional model. Such methods are known and, for example, are described in the article by Paul D. Morris et al.: "Virtual (Computed) Fractional Flow Reserve—Current Challenges and Limitations" in JACC: Cardiovascular Interventions, Vol. 8, No. 8, 2015, pages 1009 to 1117. Other calculation methods for a virtual FFR value are also known.

The approaches to the virtual calculation of the fractional flow reserve may be split into two groups. Non-invasive methods, in which geometric information about the body vessel segment or body vessel is obtained by computed tomography (CT), magnetic resonance tomography, or other methods, and minimally invasive methods in which the geometric information is obtained in the cardiac catheterization laboratory by injecting contrast medium into the vessel and then taking an X-ray. Generally, a non-invasive examination is initially performed on a patient using computed tomography. In addition to the diagnostic information about one or more vascular cross-sections of the examined body vessel segment or body vessel, a virtual value may be calculated for the fractional flow reserve, which is referred to as the CT-FFR value below. In contrast, a virtual value for a fractional flow reserve that, for example, is determined by angiography in the cardiac catheterization laboratory is referred to as the angio-FFR value below.

The CT-FFR method (e.g., the calculation of the virtual FFR value by CT) has the advantage that a three-dimensional model of the entire vascular tree in which the body vessel or the body vessel segment containing the stenosis is located is available. The CT-FFR method also enables the proper determination of the perfused myocardial mass and the perfusion flow derived from the portion of the perfused myocardial mass. Additional information such as, for example, a composition of the stenosis or of the plaque may also be determined. A disadvantage of this is the comparatively low spatial resolution and thus an inaccurate geometric representation of the stenosis geometry.

In comparison, the angio-FFR method (e.g., the calculation of a virtual FFR value using angiography) has the advantage of good spatial resolution that permits an accurate representation of the stenosis geometry. A disadvantage of this is the estimation of the blood flow using the vascular cross-sections. Even small errors here may have major consequences. Estimating the blood flow using contrast medium dynamics in the angio-FFR method is also laborious and difficult. Another disadvantage is that the angio-FFR method does not provide any information on a status of the myocardial mass, which is important, for example, in order to be able to detect any pre-existing damage and to take account of the information during treatment. Geometric information about the entire vascular tree may only be obtained with great difficulty, in part due to the relatively small detectors normally used in angiography.

For the angio-FFR method, procedures or methods of calculating a virtual FFR value are now known from the field of machine learning. Also used as inputs are geometric features of the affected body vessel segment or body vessel that is, for example, afflicted by a stenosis. These geometric features may be extracted from several segmented two-dimensional angiographies or recordings or a likewise segmented three-dimensional angiography or a reconstruction of the body vessel segment. The accuracy of the virtual FFR value depends heavily on the accuracy of the segmentation or the accuracy of the three-dimensional reconstruction. Hence, a three-dimensional reconstruction or model that is generated from several (e.g., two or more) two-dimensional angiographies or recordings may be provided. Thus, in the three-dimensional reconstruction, a higher spatial resolution may be achieved, and the geometric features may be determined more accurately as local geometric features of the affected body vessel segment.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a clinical characteristic of a body vessel segment is accurately with a low radiation dose for the patient.

A method for determining a clinical characteristic of a body vessel segment (e.g., a coronary artery) includes providing (e.g., a first provision) a three-dimensional reconstruction of a body vessel containing the body vessel segment to a computing device. At least one segmented angiography recording (e.g., two or more segmented angiography recordings) of the body vessel segment is provided (e.g., a second provision) to the computing device. The angiography recording may, for example, include a two-dimensional or a three-dimensional angiography recording. The angiography recording may also include an angiography recording of the body vessel containing the body vessel segment.

For example, the body vessel segment may have an affection (e.g., a stenosis). The provision of the at least one segmented angiography recording may also relate to an initially unsegmented angiography recording, which is then segmented by the computing device. In this case, the segmented angiography recording is provided to the computing device and is then provided by the computing device itself. The term segmentation may be an assignment of attributes (e.g., an association with the body vessel or the body vessel segment or other parts of a body associated with the body vessel) of respective picture elements of the angiography recording (e.g., of respective pixels or voxels).

Part of the method is also a first extraction by the computing device of at least one global feature of the body vessel (e.g., one or more global features of the body vessel) from the three-dimensional reconstruction. The term global feature of the body vessel may be a feature that relates to the vascular tree of the body vessel. The term vascular tree may be a unit superordinate to a vascular branch containing the body vessel segment. Likewise, part of the method is a second extraction, by the computing device, of at least one local feature of the body vessel segment (e.g., one or more local features of the body vessel segment) from the angiography recording. The term local feature of the body vessel segment may be a feature that relates to the vascular branch containing the body vessel segment. For example, the local feature may also relate to an attribute of a stenosis in the body vessel segment (e.g., may represent an attribute of the stenosis). The clinical characteristic is determined for the body vessel segment as a function of the extracted local feature and of the extracted global feature. This may, for example, be done by the computing device (e.g., semi-automatically or fully automatically).

The advantage of this is that the angiography recording need merely be created for the body vessel segment, but not for the whole body vessel that includes the body vessel segment. Information about the larger body vessel may still be taken into account when calculating or determining the clinical characteristic. Thus, the reconstruction of the whole body vessel (e.g., a complete vascular tree) that otherwise might take place as part of the angiography, which is laborious and difficult and uses more than two recordings, may be omitted. Thus, a radiation dose for a corresponding patient is reduced, but yet, at the same time, the complete vascular tree is taken into account in the form of the at least one global feature when determining the clinical characteristic. Thus, accuracy is preserved or even increased. For example, an angio-FFR value may be calculated in this way, in which the global feature or features are used to take account of the association with additional branches in the entire vascular tree, whereas the local feature or features provide the accurate details for a stenosis in the vascular branch (e.g., the body vessel segment).

In an embodiment, the angiography recording and the three-dimensional reconstruction are registered to one another. The term registration may be in the sense of an image registration, in which the three-dimensional reconstruction is placed into a defined, unambiguously determined spatial relationship to the angiography recording in order to bring the body vessel segment in the three-dimensional reconstruction into spatial concordance with the body vessel segment in the angiography recording. In this way, a picture element in the three-dimensional reconstruction may be assigned to each picture element in the angiography in a mathematically one-to-one manner.

The advantage of this is that the local and the global feature stand in a defined spatial relationship to one another. For example, in the case of geometric features, the local and the global feature may be better linked to one another in this way in order to increase the accuracy when determining the clinical characteristic. Additionally, a global feature may be inspected using a local feature or vice versa. This contributes to increased accuracy. Errors that may otherwise arise because of an incorrect assignment are ruled out in this way (e.g., the assignment of the body vessel segment to an incorrect region of the body vessel).

In a further embodiment, the clinical characteristic includes a hemodynamic characteristic or a hemodynamic parameter. For example, the clinical characteristic may include a value of a fractional flow reserve of the body vessel segment, an FFR value, and/or an instantaneous pressure ratio for the body vessel segment, and/or an instantaneous wave-free ratio (iFR) for the body vessel segment, and/or a pressure ratio for the body vessel segment or a pressure ratio between a distal pressure and an aortic pressure for the body vessel segment, and/or a blood flow through the body vessel segment, and/or a blood pressure in the body vessel segment, and/or a wall shearing force in the body vessel segment. The method described is advantageous for the cited hemodynamic characteristic, as for the determination, a particularly high degree of accuracy is to be provided in the spatial resolution of the angiography. Thus, the combination of the local features on the angiography with the global features from the three-dimensional reconstruction often obviates the need for additional X-ray recordings, without any loss of accuracy. Alternatively, accuracy may be increased even without an additional radiation dose by transferring the global feature from the three-dimensional reconstruction.

In a further embodiment, the global feature includes a geometric feature of the body vessel, and/or a physiological feature of the body vessel, and/or a structural feature of the body vessel. The global feature may, for example, also include a combination of several features (e.g., several of the cited features). The geometric feature may, for example, be a length (e.g., of the body vessel or of a part of the body vessel), and/or a length ratio (e.g., of the body vessel or of a part of the body vessel to another part of the body vessel), and/or a diameter (e.g., of the body vessel or of a part of the body vessel), and/or a diameter ratio (e.g., of the body vessel or of a part of the body vessel to another part of the body vessel or to another body vessel), and/or an angle (e.g., an angle between different regions or parts of the body vessel). The physiological feature may, for example, include a flow resistance of the body vessel, and/or a flow through the body vessel, and/or a variable of a myocardial tissue. The structural feature may, for example, include a number of ramifications in the body vessel, and/or a type of ramifications, and/or a spacing of the ramifications, and/or a ramification angle of the ramifications. With one or more of the cited geometric and/or physiological and/or structural features as a global feature, clinical characteristics may be calculated particularly accurately in combination with the local feature.

In a further embodiment, the local feature includes a geometric feature of the body vessel segment, and/or a physiological feature of the body vessel segment, and/or a structural feature of the body vessel segment. The local feature may, for example, also include a combination of several features (e.g., several of the cited features). The geometric feature may, for example, include a length (e.g., of the body vessel segment or of a part of the body vessel segment), and/or a length ratio (e.g., of the body vessel segment or of a part of the body vessel segment to another part of the body vessel segment), and/or a diameter (e.g., of the body vessel segment or of a part of the body vessel segment), and/or a diameter ratio (e.g., of the body vessel segment or of a part of the body vessel segment to another part of the body vessel segment), and/or an angle between different parts of the body vessel segment. The physiological feature of the body vessel segment may, for example, include a flow resistance of the body vessel segment, and/or a blood flow through the body vessel segment, and/or a variable of a myocardial tissue. The structural feature of the body vessel segment may, for example, include a number of stenoses in the body vessel segment, and/or a composition of a plaque of the stenosis or of the stenoses, and/or a spacing of the stenoses, and/or a geometric dimension of the stenosis or of the stenoses (e.g., a length, and/or, a width and/or a height, and/or an internal diameter, and/or an external diameter of the stenosis or of the stenoses). The body vessel segment may thus, for example, have a stenosis. The cited geometric, physiological, and/or structural features have the advantage, as a local feature of the body vessel segment, that the clinical characteristic may be calculated particularly well in combination with the global feature. The choice of one or more matching features permits, for example, a particularly complication-free integration of the features into a calculation of the clinical characteristic and thus opens up other advantages such as, for example, a particularly simple determination of the clinical characteristic.

In an embodiment, the three-dimensional reconstruction is generated using an imaging method different from angiography. Different recording modalities may therefore be used. For example, the three-dimensional reconstruction may be generated using computed tomography and/or magnetic resonance tomography. The advantage of this is that by using the global feature, it is possible to take account of information that is less easily obtained or extractable or determinable by angiography when determining or calculating the clinical characteristic or information that may influence the determination and thus the clinical characteristic. In one embodiment, computed tomography or magnetic resonance tomography is used, as these permit a recording of an entire vascular tree (e.g., a larger body vessel), whereas angiography is typically suitable for a high-resolution recording of a very small and restricted recording region such as a body vessel segment or vascular branch as part of the body vessel or body vascular tree. Computed tomography is often created in advance, so that here, by using existing computed tomography, the need for a radiation dose may be obviated particularly easily, and nevertheless, the relevant information may be extracted in the form of the global feature and taken into account in the improved calculation of the clinical characteristic.

In a further embodiment, the determination of the clinical variable is performed by the computing device using machine learning or a machine learning method. The global feature and the local feature are used as a basic condition for one or more calculation steps during the machine learning. The advantage of this is that the determination of the clinical variable may be performed particularly flexibly in a large number of cases automatically (e.g., fully automatically). Alternatively, other hemodynamic calculation methods may also be used to determine the clinical variable. In this case, for example, geometric information may be used via the local feature or the global feature, and other basic conditions for determining the clinical variable may be extracted from the other feature (e.g., the global or local feature).

In a further embodiment, a value of the global feature is adjusted as a function of a value of the local feature (e.g., an accuracy of the global feature is increased by the local feature), or a value of the local feature is adjusted as a function of the global feature (e.g., an accuracy of the local feature is increased as a function of the global feature). The features may therefore be used to update the features reciprocally or to improve accuracy. This may take place, for example, using simple statistical methods or using other mathematical correlations of the respective values of the features.

The choice of homogeneous features is favorable in this case. It may be provided that the at least one local and the at least one global feature in each case includes a homogeneous geometric and/or physiological and/or structural feature. To increase the accuracy of the values for the respective features, the local feature is compared to the global feature, and based on a result of the comparison or correlation, the values for the respective features are aligned or adjusted to one another. This has the advantage that a redundancy of available information from the three-dimensional reconstruction and the angiography is used for an improved accuracy of the clinical characteristic determined.

In an embodiment, a segmented angiography recording of a further body vessel segment is provided (e.g., a third provision) to the computing device, at least one local feature of the further body vessel segment is extracted by the computing device, and the clinical variable of the body vessel segment is determined. The provision, the extraction, and the determination take place as a function of the local feature of the further body vessel segment. The determination may also be performed by the computing device. The further body vessel segment may also be provided in the same angiography recording as the one body vessel segment that is described hitherto. Thus, the provision may take place via a provision of the same segmented angiography recording as the first provision described above. In an embodiment, the provision of the segmented angiography recording of the further body vessel segment, however, relates to a segmented further angiography recording different from the one segmented angiography recording of the second provision discussed above. The advantage of this is that if, for example, several serial or parallel stenoses are present in a vascular branch or body vessel segment, which cannot be represented in angiography with sufficient accuracy, an overall value for the clinical variable (e.g., an overall FFR value) may be calculated in this way with great accuracy and low radiation exposure using the local features of several angiography recordings or segmentations within an angiography recording. This may be done by linking the respective local feature to the global feature or the global calculation variable to an overall feature model or an overall calculation model.

In one embodiment, the one body vessel segment or the further body vessel segment includes a further stenosis different from the one stenosis.

One or more of the present embodiments also include an examination system for determining a clinical characteristic of a body vessel segment. The examination system includes an imaging medical device (e.g., a computed tomography system) for the provision of a three-dimensional reconstruction of a body vessel containing the body vessel segment, and an angiography device for the provision of a segmented angiography recording of the body vessel segment. The examination system also includes a computing device that may be coupled to the imaging medical device and to the angiography device for the transfer of information. The computing device is configured to extract at least one global feature of the body vessel from the three-dimensional reconstruction, and to extract at least one local feature of the body vessel segment from the angiography recording. The computing device is also configured to determine a clinical variable of the body vessel segment as a function of the extracted local feature and the extracted global feature.

Advantages and advantageous embodiments of the examination system correspond to advantages and advantageous embodiments of the method.

The features and combinations of features cited above in the description, and the features and combinations of features cited below in the description of the figures and/or shown alone in the FIGURE may be used not only in the respectively specified combination, but also in other combinations, without departing from the scope of the invention. Thus, embodiments of the invention that are not explicitly shown and explained in the FIGURES but that emerge from and may be generated from the embodiments explained thanks to separate combinations of features are also to be regarded as included and disclosed. Embodiments and combinations of features that thus do not have all features of an originally worded independent claim are also to be regarded as disclosed. In addition, embodiments and combinations of features (e.g., due to the embodiments set forth above) that go further than or deviate from the combinations of features set forth in the related claims are also to be regarded as disclosed.

BRIEF DESCRIPTION OF THE DRAWINGS

FIG. 1 shows a schematic flow diagram of an exemplary embodiment of a method for determining a clinical characteristic of a body vessel segment.

DETAILED DESCRIPTION

In the method represented in FIG. 1, a computing device identifies (e.g., is provided) a three-dimensional reconstruction of a body vessel (e.g., a coronary artery) in a first act. The body vessel includes, for example, a complete body vascular tree of the coronary artery and also has a body vessel segment (e.g., a vascular branch). In the example shown, the body vessel segment is a body vessel segment of the coronary artery with a stenosis. The three-dimensional reconstruction of the body vessel containing the body vessel segment is generated using, for example, a computed tomography system or computed tomography.

The computing device identifies (e.g., is provided) an angiography (e.g., a segmented angiography) of the body vessel segment (e.g., of the vascular branch of the coronary artery with the stenosis) in a next act 2. In the present case, a further act is to register 3 the angiography recording to the three-dimensional reconstruction. Thus, a corresponding picture element or voxel of the three-dimensional reconstruction is assigned to one or more picture elements or pixels of the angiography. Further picture elements of the angiography may thus be assigned to further picture elements of the three-dimensional reconstruction and vice versa.

At least one global feature (e.g., several global features of the body vessel) that relates to the vascular tree is extracted 4 from the three-dimensional reconstruction by the computing device. In one embodiment, a global geometric feature in the form of a diameter of the body vessel or body vascular tree is extracted. As a global physiological feature, a variable of a myocardial tissue of the coronary artery is extracted. As a global structural feature of the body vessel, a number of ramifications in the body vessel, the nature of the ramifications, and the spacing of the ramifications are extracted.

At least one local feature (e.g., several local features of the body vessel segment) that relates to the vascular branch that, for example, has the stenosis is extracted 5. A diameter of the body vessel segment is extracted as a local geometric feature of the body vessel segment. As a local physiological feature, a flow resistance of the body vessel segment is extracted. As a local structural feature, a number of stenoses in the body vessel segment, a spacing of the stenoses, and a respective geometric dimension of the stenosis are extracted.

An adjustment 6 of a value of the global feature takes place as a function of a value of the local feature (e.g., an adjustment of the diameter of the body vessel to the diameter of the body vessel segment). For this, the homogeneous geometric feature (e.g., the diameter of the body vessel) is used as a global feature, and the diameter of the body vessel segment is used as a local feature in a comparison 7 in order to increase the accuracy of the three-dimensional reconstruction in the region of the body vessel segment.

Thus, for example, in the present case of two serial or parallel stenoses, which are not clearly separated in the three-dimensional reconstruction, a local, more accurate knowledge of the diameter of the body vessel segment may be used to improve the three-dimensional reconstruction.

The clinical characteristic to be determined as, for example, an FFR value for the body vessel segment is determined 8 as a function of the extracted local and global features. For example, the determined diameters and the determined myocardial mass, the flow resistance and the attributes of the determined ramifications, as well as of the determined stenoses may be used as basic conditions for machine learning or another known hemodynamic calculation method.

Very accurate information about the local features in the body vessel segment affected by the stenosis may be utilized in relation to the stenosis, and at the same time, global information about the vascular tree or the body vessel containing the body vessel segment may be taken into account without further X-ray recordings (e.g., without an additional radiation dose being necessary) in order to achieve a particularly accurate calculation of the clinical characteristic (e.g., the FFR value).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a clinical characteristic of a body vessel segment, the method comprising:
   identifying a three-dimensional reconstruction of a body vessel containing the body vessel segment;
   identifying a segmented angiography recording of the body vessel segment to a computing device;
   extracting, by the computing device, at least one global feature of the body vessel from the three-dimensional reconstruction;
   extracting, by the computing device, at least one local feature of the body vessel segment from the segmented angiography recording; and
   determining the clinical characteristic for the body vessel segment as a function of the at least one extracted local feature and the at least one extracted global feature,
   wherein the determining of the clinical characteristic by the computing device comprises machine learning, and wherein the at least one global feature and the at least one local feature are used as a basic condition for one or more computing steps during the machine learning.

2. The method of claim 1, wherein the segmented angiography recording and the three-dimensional reconstruction are registered to one another.

3. The method of claim 1, wherein the clinical characteristic comprises a hemodynamic characteristic, an instantaneous pressure ratio for the body vessel segment, an instantaneous wave-free ratio for the body vessel segment, a pressure ratio between a distal pressure and an aortic pressure for the body vessel segment, a blood flow through the body vessel segment, a blood pressure in the body vessel segment, a wall shearing force in the body vessel segment, or any combination thereof.

4. The method of claim 3, wherein the hemodynamic characteristic comprises a value of a fractional flow reserve of the body vessel segment.

5. The method of claim 1, wherein the at least one global feature comprises a geometric feature of the body vessel, a physiological feature of the body vessel, a structural feature of the body vessel, or any combination thereof.

6. The method of claim 5, wherein the at least one global feature comprises the geometric feature of the body vessel, the geometric feature of the body vessel comprising a length, a diameter, an angle, or any combination thereof.

7. The method of claim 5, wherein the at least one global feature comprises a physiological feature of the body vessel, the physiological feature comprising a flow resistance of the body vessel, a blood flow through the body vessel, a variable of a myocardial tissue, or any combination thereof.

8. The method of claim 5, wherein the at least one global feature comprises a structural feature of the body vessel, the structural feature comprising a number of ramifications in the body vessel, a nature of the ramifications, a spacing of the ramifications, a ramification angle of the ramifications, or any combination thereof.

9. The method of claim 1, wherein the at least one local feature comprises a geometric feature of the body vessel segment, a physiological feature of the body vessel segment, a structural feature of the body vessel segment, or any combination thereof.

10. The method of claim 9, wherein the at least one local feature comprises the geometric feature of the body vessel segment, the geometric feature comprising a length, a diameter, an angle, or any combination thereof.

11. The method of claim 9, wherein the at least one local feature comprises a physiological feature of the body vessel segment, the physiological feature comprising a flow resistance of the body vessel segment, a blood flow through the body vessel segment, a variable of a myocardial tissue, or any combination thereof.

12. The method of claim 9, wherein the at least one local feature comprises a structural feature of the body vessel segment, the structural feature comprising a number of stenoses in the body vessel segment, a composition of a plaque of the stenoses, a spacing of the stenoses, a geometric dimension of the stenosis or stenoses, or any combination thereof.

13. The method of claim 1, wherein the three-dimensional reconstruction is generated using an imaging method different from angiography.

14. The method of claim 13, wherein the imaging method different from angiography comprises computed tomography or magnetic resonance tomography.

15. The method of claim 1, further comprising adjusting a value of the at least one global feature as a function of a value of the at least one local feature or adjusting a value of the at least one local feature as a function of the at least one global feature.

16. The method of claim 15, wherein each of the at least one local feature and the at least one global feature each comprises a homogeneous geometric feature, a physiological feature, a structural feature, or any combination thereof,
wherein the computing device is configured to:
compare the at least one local feature to the at least one global feature; and
adjusting values for respective features of the at least one local feature and the at least one global feature to one another based on a result of the comparison.

17. The method of claim 1, further comprising:
providing a segmented angiography recording of a further body vessel segment a to the computing device; and
extracting, by the computing device, at least one local feature of the further body vessel segment,
wherein determining the clinical characteristic for the body vessel segment comprises determining the clinical characteristic for the body vessel segment as a function of the at least one local feature of the further vessel segment.

18. An examination system for determining a clinical characteristic of a body vessel segment, the examination system comprising:
an imaging medical device configured to provide a three-dimensional reconstruction of a body vessel containing the body vessel segment;
an angiography device configured to provide a segmented angiography recording of the body vessel segment; and
a computing device that is coupleable to the imaging medical device and the angiography device, the computing device being configured to:
extract at least one global feature of the body vessel from the three-dimensional reconstruction; and
extract at least one local feature of the body vessel segment from the segmented angiography recording; and
determine a clinical variable of the body vessel segment as a function of the at least one extracted local feature and the at least one extracted global feature,
wherein the computing device is configured to determine the clinical variable with machine learning, and
wherein the at least one global feature and the at least one local feature are used as a basic condition for one or more computing steps during the machine learning.

* * * * *